(12) United States Patent
Harris, Jr. et al.

(10) Patent No.: US 8,128,585 B2
(45) Date of Patent: Mar. 6, 2012

(54) VIBRATION DAMPENING DEVICE AND METHOD

(75) Inventors: Charles F. Harris, Jr., New Castle, DE (US); John E. Garnier, Newark, DE (US)

(73) Assignee: Wristband Enterprises LLC, New Castle, DE (US)

( * ) Notice: Subject to any disclaimer, the term of this patent is extended or adjusted under 35 U.S.C. 154(b) by 362 days.

(21) Appl. No.: 10/734,322

(22) Filed: Dec. 12, 2003

(65) Prior Publication Data
US 2005/0131322 A1    Jun. 16, 2005

(51) Int. Cl.
*A61F 5/00* (2006.01)
*A61F 13/00* (2006.01)

(52) U.S. Cl. ............... 602/20; 602/21; 602/62

(58) Field of Classification Search .......... None
See application file for complete search history.

(56) References Cited

U.S. PATENT DOCUMENTS

| | | | |
|---|---|---|---|
| 3,403,429 A * | 10/1968 | Smith | 24/306 |
| 3,586,001 A * | 6/1971 | Sanderson | 606/203 |
| 4,014,327 A | 3/1977 | Spiro | |
| 4,048,991 A | 9/1977 | Marx | |
| 4,628,918 A * | 12/1986 | Johnson, Jr. | 602/13 |
| 4,759,963 A * | 7/1988 | Uso et al. | 428/100 |
| 5,338,290 A | 8/1994 | Aboud | |
| 5,441,058 A | 8/1995 | Fareed | |
| 5,466,215 A | 11/1995 | Lair et al. | |
| 5,478,306 A | 12/1995 | Stoner | |
| 5,865,775 A | 2/1999 | Peoples et al. | |
| 5,901,379 A | 5/1999 | Hirata | |
| 5,921,949 A | 7/1999 | Dray | |
| 5,971,947 A | 10/1999 | McNally et al. | |
| 6,120,472 A | 9/2000 | Singer, Jr. | |
| 6,149,617 A | 11/2000 | McNally et al. | |
| 6,149,618 A | 11/2000 | Sato | |
| 6,213,969 B1 | 4/2001 | MacMorran et al. | |
| 6,361,549 B1 | 3/2002 | Asatourian et al. | |
| 6,398,749 B1 * | 6/2002 | Slautterback | 602/62 |
| 6,399,852 B1 | 6/2002 | Barron | |
| 6,478,760 B2 * | 11/2002 | Darcey | 602/20 |
| 6,517,507 B1 | 2/2003 | Faherty | |
| 6,565,524 B1 | 5/2003 | Itonaga et al. | |
| 6,582,449 B2 | 6/2003 | Grey et al. | |
| 6,585,674 B2 | 7/2003 | Toda | |
| 2003/0032912 A1 | 2/2003 | Weaver, II et al. | |
| 2003/0045826 A1 * | 3/2003 | Meyer | 602/62 |

* cited by examiner

*Primary Examiner* — Jack W. Lavinder
(74) *Attorney, Agent, or Firm* — Patricia S. Rogowski; Donald W. Huntley; Jeffrey R. Ramberg

(57) ABSTRACT

A vibration dampening device includes a strap or band wrapped around a human body part. The strap includes one or more wing sections, either integrally formed or engaged thereto, that extend beyond the nominal width of the strap and have freedom of movement with respect to the strap. The distal ends of step members engaged to the strap may form wing sections. Wing section movement counteracts longitudinal vibrations traveling through soft tissue and musculature to dampen such vibrations. Optionally, a tension limiter may be provided to help maintain wrapping tension at or below a desired level, such as 3 pounds-force or below, which applied at a strap area of 0.093 square inches is about 32 psi.

46 Claims, 4 Drawing Sheets

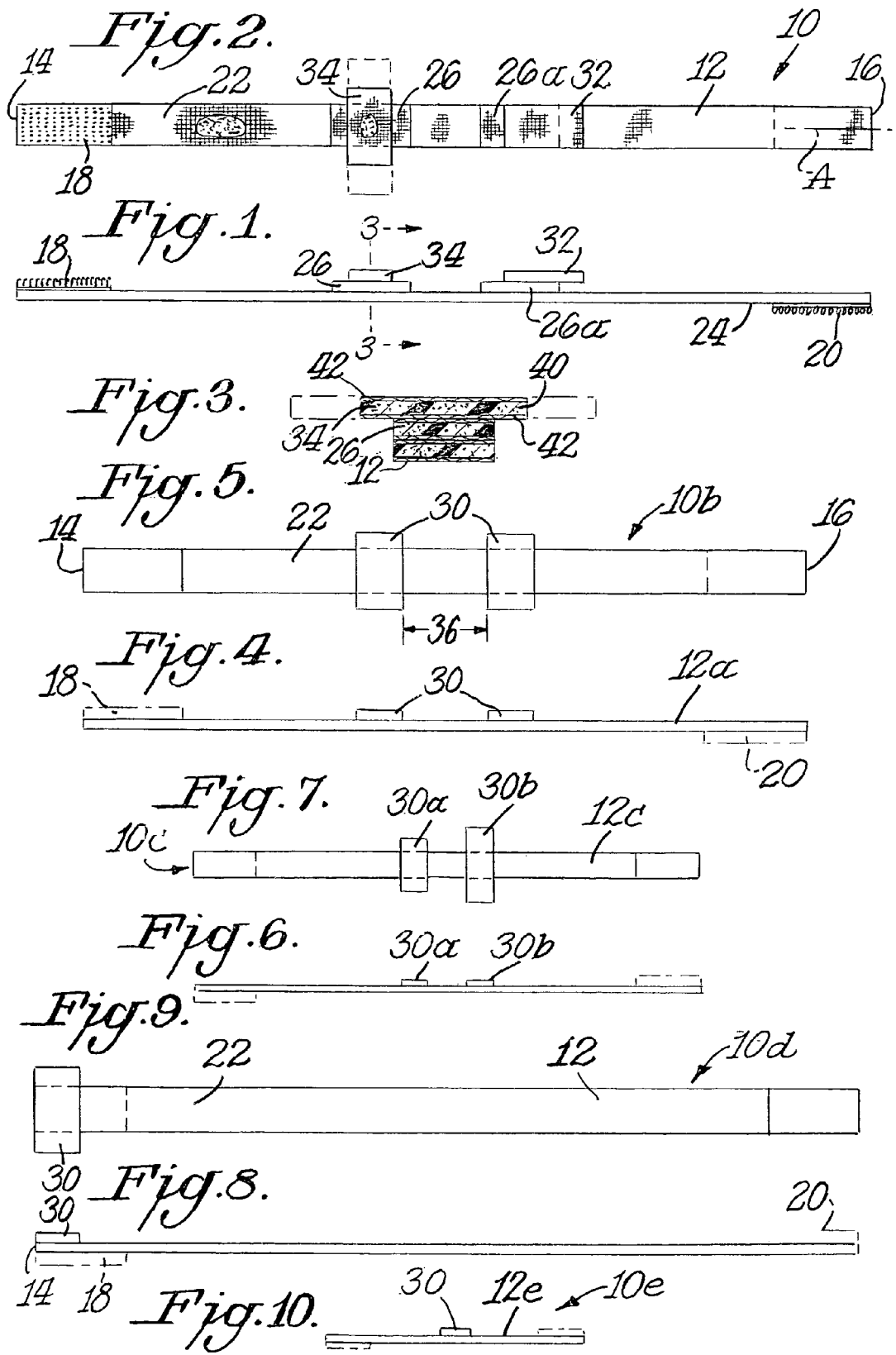

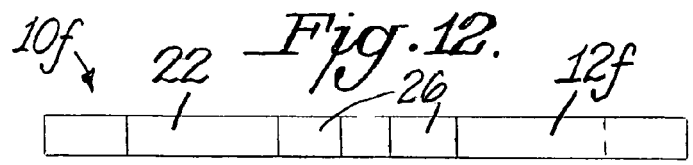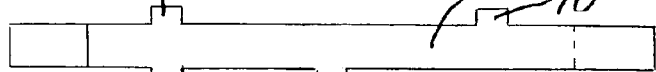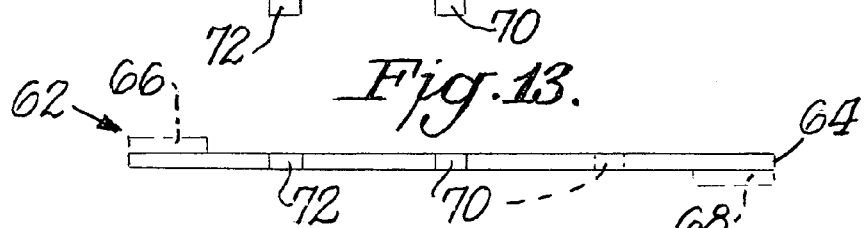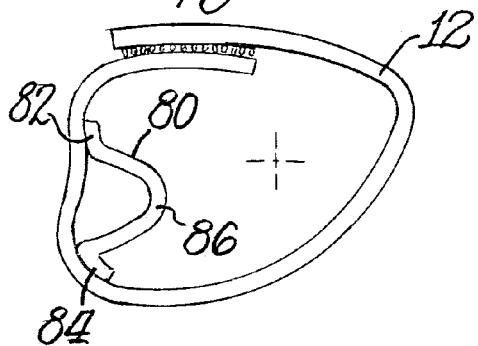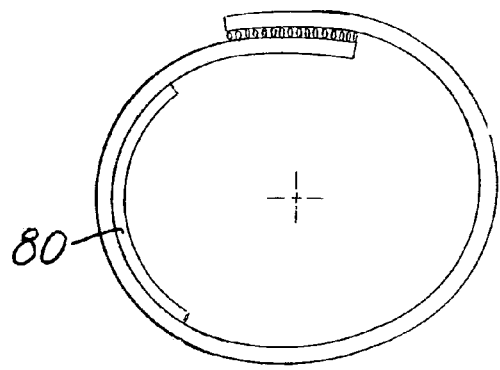

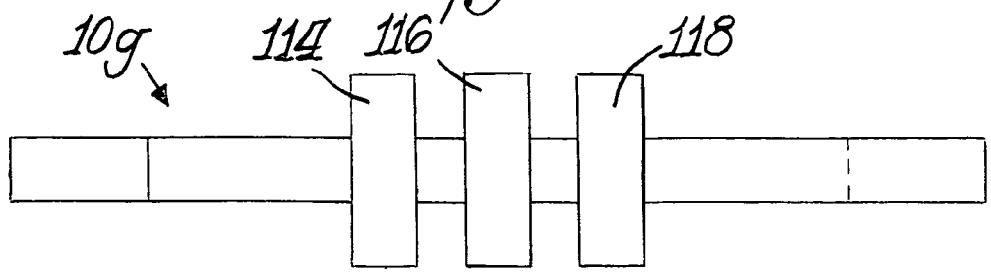
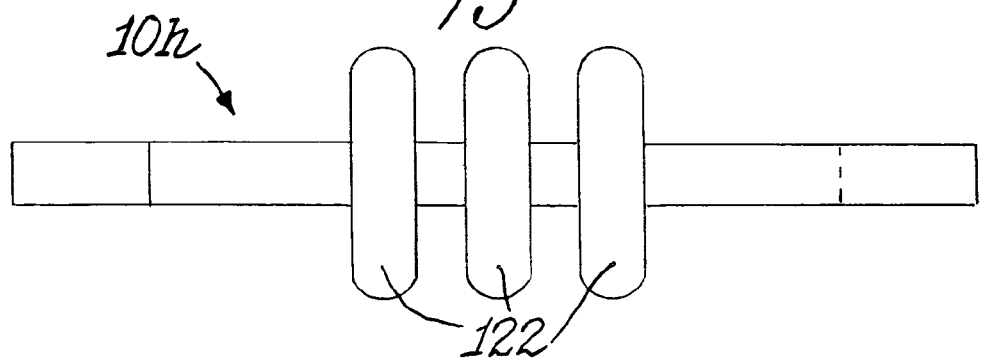
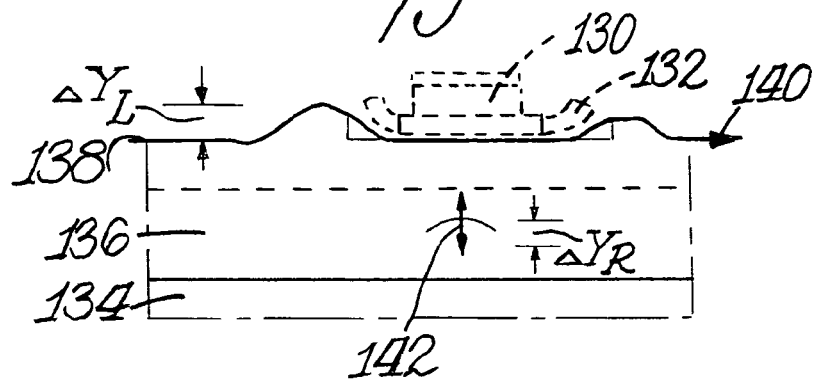

VIBRATION DAMPENING DEVICE AND METHOD

FIELD OF INVENTION

The present invention relates to a vibration dampening strap or band that is engaged around a person's torso, arm, leg, neck, or other extremity at a suitable tension to dampen vibration of musculature and soft tissue thereby preventing possible injury or pain that would otherwise result from repeated muscle and soft tissue vibration.

BACKGROUND OF THE INVENTION

Impact-induced vibrations that travel along a human body part may lead to muscle or joint fatigue, or even injury. For example, a vibrating tennis racket held in the hand will transmit longitudinally and radially traveling vibrations into the hand, wrist, elbow, upper arm and shoulder. For some, these repeated vibrations lead to a painful injury termed "tennis elbow".

Several methods for isolating or reducing vibrations are discussed in the prior art. For example, a dampening device containing one or more springs may be attached directly to racket strings to try to dampen string-induced vibrations before the vibrations reach the racket handle. While effective to some degree, such devices do not completely eliminate vibrations from being transmitted to the hand, wrist, forearm, elbow, etc.

An alternative vibration reducing method is to apply a vibration absorber to the vibration source (sometimes termed an "active" or "dynamic" vibration absorber). Dynamic vibration absorbers use a mass-spring combination that can be tuned to exert a force equal and opposite to a sensed vibration. Dynamic vibration absorbers require an electronic power source and are not considered practical for use in racket sports.

Yet another alternative is a "passive" vibration absorber, which incorporates mechanical means such as a mass-spring-fluid combination, to dampen excessive unwanted vibrations. To be effective, passive vibration absorbers require a means to apply a counter force to a vibration, such as with automobile shock absorbers that have a spring, a piston and fluid forced by the piston from one chamber into another chamber.

A number of supports and braces have been proposed for use to treat "tennis elbow" and other impact-induced shock on the human elbow joint. For example, U.S. Pat. No. 5,865,775 discloses a forearm sleeve 10 with an energy-attenuating viscoelastic means 50 affixed to such sleeve. A tension strap 32 is wrapped around the sleeve to counter-forces directed-radially outwardly from the sleeve and the viscoelastic means 50. Such sleeve and band combination purports to dampen vibrations emanating radially outwardly from the bone to the outer skin of the arm, but has no effect on vibrations of soft tissue, particularly vibrations emanating longitudinally or along the length of the arm.

U.S. Pat. No. 6,149,617 discloses a tennis elbow band that incorporates a removable thermal packet 20 therein. The thermal packet may be heated or chilled before it is inserted into the band. The band with thermal packet therein is tightened around a wearer's forearm to apply pressure and in combination with heating or cooling (if the thermal packet has been heated or chilled). The band has no effect on minimizing or dampening vibrations of soft tissue which travel in a longitudinal direction along a wearer's arm.

U.S. Pat. No. 5,338,290 shows a variable tension band formed as a laminate with multiple strips of elastic material 11 attached to one another with reinforcing ribs 13. The band is wrapped around a body part with sufficient tension to relieve pain. The ends of the band are joined together with hook and loop fasteners 12a, 12b. The patent indicates that joint pain may be relieved by wrapping the band around a body part at least one inch away from the joint. The band has no effect on vibrations which travel in a longitudinal direction along a wearer's arm or along a wearer's leg.

Bands have also been proposed for wrapping about the wrist to support the carpals and aid in preventing or treating carpal tunnel syndrome. See, e.g. U.S. Pat. Nos. 5,478,306 and 6,517,507. Such bands tightly encircle the wrist, but have no means for dampening vibrations of soft tissue which travel in a longitudinal direction from the hand across the wrist and along the wearer's arm.

U.S. Pat. No. 5,921,949 discloses a carpal tunnel wrist corrective support formed as a flexible strap with an inner surface onto which at least two compression pads are removably applied. The compression pads 41 and 42 are shown aligned with their major axis perpendicular to the longitudinal axis of the strap. The compression pads are fully adhered to the inner surface with hook and loop fasteners provided over the entire pad surface. There is no portion of a compression pad extending outwardly from the edges of the strap or left to freely vibrate without connection to the strap. Hence the strap has no means for dampening vibrations of soft tissue which travel in a longitudinal direction from the hand across the wrist and along the wearer's arm.

U.S. Pat. No. 6,585,674 shows a stretchable band having a wedge-shaped foam piece 14 adhered to one surface. The wedge-shaped foam piece supports a wearer's foot while the band is wrapped around the wearer's ankle. The band and wedge are intended to better align a wearer's foot and ankle to minimize injury to the knee. No means are provided for dampening vibrations of soft tissue which travel in a longitudinal direction from the foot across the ankle and along the wearer's leg.

Effective means for isolating and/or reducing impact-induced vibrations from traveling longitudinally along soft tissue of human extremities are still sought.

SUMMARY OF INVENTION

In a first aspect of the invention, a vibration dampening device for wrapping a human body part, such as an arm, wrist, ankle, leg, finger, toe, chest, torso or neck, has a strap having a nominal width and length and having a body contacting surface and an outer surface. The strap may be formed as a continuous band of stretchable material or may have a proximal end and a distal end with a fastener provided at one or both ends. A preferred fastener is a hook and loop fastener (VELCRO®) that may be adjustably engaged to provide different wrapping tension. When wrapped around a human body part, preferably the strap exerts a tension of no more than 5 pounds-force (applied at a strap area of 0.093 square inches this translates to 53 pounds per square inch) on said body part, most preferably no more than 3 pounds-force (applied at a strap area of 0.093 square inches this translates to 32 pounds per square inch).

Preferably, the strap is formed from neoprene, polyethylene, polyurethane or spandex. Most preferably, the strap is covered with a woven or nonwoven fabric or felt so that the strap may be comfortably worn in contact with the skin. The preferred material forming the strap is a viscoelastic material having a density in the range of 7 to 15 pounds per cubic foot, a tensile strength from 40 to 80 psi, a minimum elongation of 100%, and a compression deflection at 25% of from 3 to 10 psi.

A step member is engaged to the strap, such as with an adhesive. The step member has a length and a width, and the length of said step member is longer than the width of said step member, and longer than the width of the strap. Where the strap defines a central axis and the step member defines an axis along its length, preferably the step member is engaged to the body contacting surface of the strap so that its axis is substantially perpendicular to the axis of the strap. Alternatively, the step member may be attached to the outer surface of the strap.

The step member has a proximal end and a distal end, and defines a first wing portion at its distal end and a second wing portion at its proximal end. In one embodiment, the first wing portion extends beyond the width of the strap when the step member is engaged to the strap. In another embodiment, the step member defines an axis along its length, and said step member is engaged to the body contacting surface of the strap so that its axis is either parallel to or generally aligned with the axis of the strap. The outer peripheries of the wing portions of step members may vary in shape, including straight, curved, or other regular or irregular shape or any combination of such shapes.

More than one step member may be engaged to the strap. In one preferred embodiment, the step members are formed of the same materials as the strap. More preferably, when at least one additional step member is engaged to the body contacting surface of the strap, such additional step member is formed of a different material than the material of the other step member(s) so that the additional step member has a different modulus of elasticity and a different force constant (k). Where two or more step members are engaged to the strap, preferably they are spaced apart so as not to contact one another. A preferred gap between two step members is from 0.25 to 4.0 inches.

In another alternate embodiment, a second step member may be engaged to the first step member, with the axis of the second step member either generally aligned with the axis of the first step member, or substantially perpendicular to the axis of the first step member, or at an angle therebetween.

In yet another alternate embodiment, the strap further is provided with a tension limiter, which is a loop that has two ends and a loop portion between said ends, and wherein said ends are attached to the body contacting surface of the strap. Alternatively, the ends may be attached to the outer surface of the strap. The tension limiter helps to keep the strap tension below a defined maximum, for example, such as below 3 pounds-force (applied to a strap area of 0.093 square inches this translates to 32 psi).

When the strap is engaged, the wing portions of the step members have freedom of movement with respect to the strap. The wing portions thus direct a restorative force onto the skin to counteract vibrations that are transmitted longitudinally along the wearer's skin and soft tissue.

In still another embodiment, the strap may be formed without step members, but with integral wing members, such that the strap defines a nominal width and the wing members comprise extensions beyond said nominal width. Such wing members or extended portions of the strap still have freedom of movement such that they direct restorative force onto the skin to counteract vibrations that are transmitted longitudinally along the skin and soft tissue. Wing members may extend from equal and opposite sides of the strap and have their axes aligned, or they may be offset from one another. Such wing members may have straight or curved or other regularly or irregularly shaped outer peripheries.

As another aspect, methods for dampening longitudinal vibrations along human soft tissue and musculature use the vibration dampening straps of the invention. One or more such straps may be wrapped around a body part, such as an arm, wrist, ankle, leg, finger, toe, chest, torso or neck, at a suitable tension (such as 0.1 to 5 pounds-force, preferably 1 to 2 pounds-force) so as to dampen longitudinal vibrations of soft tissue and/or musculature.

BRIEF DESCRIPTION OF THE DRAWINGS

FIG. 1 is a side elevational view of a first embodiment of a vibration dampening strap according to the invention;

FIG. 2 is a top plan view of the strap of FIG. 1;

FIG. 3 is a cross sectional view in elevation taken along line 3-3 of FIG. 1, showing details of the strap and attached wings;

FIG. 4 is a side elevational view of a second embodiment of a vibration dampening strap according to the invention;

FIG. 5 is a top plan view of the strap of FIG. 4;

FIG. 6 is a side elevational view of a third embodiment of a vibration dampening strap according to the invention;

FIG. 7 is a top plan view of the strap of FIG. 6;

FIG. 8 is a side elevational view of a fourth embodiment of a vibration dampening strap according to the invention;

FIG. 9 is a top plan view of the strap of FIG. 8;

FIG. 10 is a side elevational view of a fifth embodiment of a vibration dampening strap according to the invention, which strap has shorter length more suited for wrapping around a finger or toe;

FIG. 11 is a side elevational view of a sixth embodiment of a vibration dampening strap according to the invention;

FIG. 12 is a top plan view of the strap of FIG. 11;

FIG. 13 is a side elevational view of a seventh embodiment of a vibration dampening strap according to the invention;

FIG. 14 is a top plan view of the strap of FIG. 13;

FIG. 15 is a side elevational view of an eighth embodiment of a vibration dampening strap according to the invention, which strap includes a tensioner and has been looped to engage hook and loop fasteners positioned at the strap ends;

FIG. 16 is a side elevational view of the strap of FIG. 15, wherein the strap has been stretched to expand the tensioner therein;

FIG. 19 is a top plan view of an eighth embodiment of a vibration dampening strap according to the invention;

FIG. 20 is a top plan view of a tenth embodiment of a vibration dampening strap according to the invention; and FIG. 21 is a schematic diagram in partial cross section showing a vibration dampening strap according to the invention wrapped about a human extremity, and illustrating the dampening of a longitudinally traveling soft tissue vibration.

DESCRIPTION OF THE PREFERRED EMBODIMENTS

Figure 17:
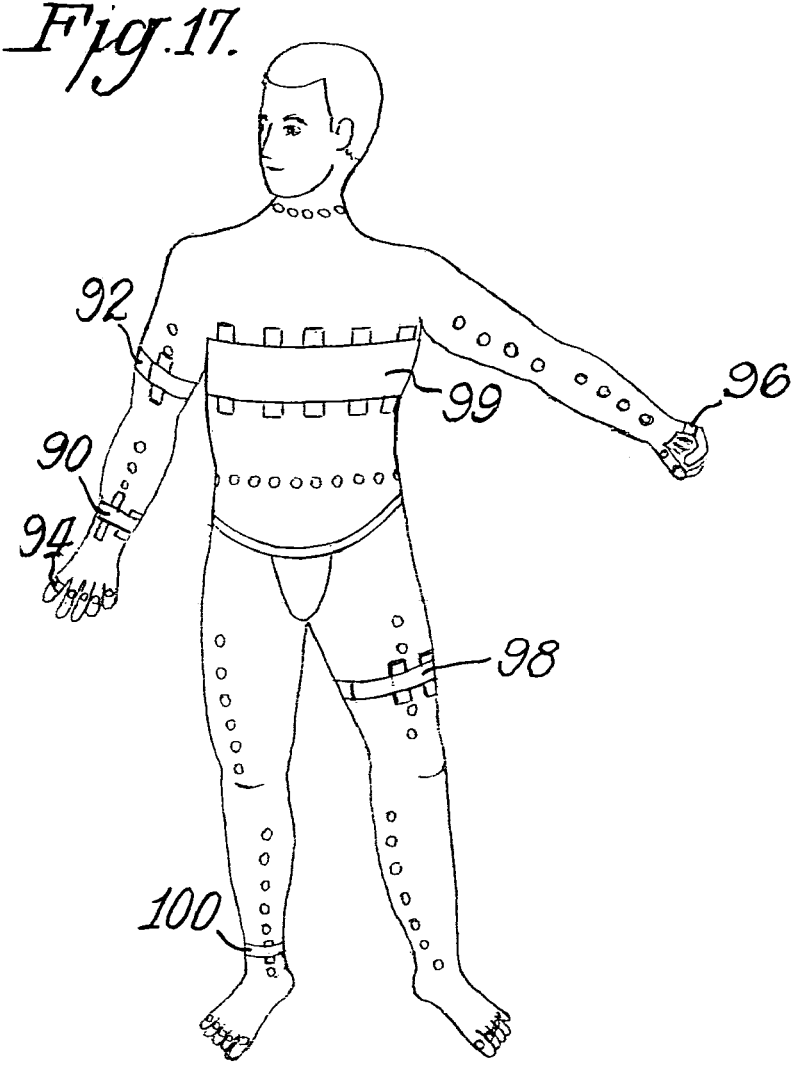
FIG. 17 is a schematic diagram of a human figure who has vibration dampening straps according to the invention attached to his upper arm, forearm, thumb, finger, thigh and ankle, and wherein further alternate locations for wrapping straps according to the invention are designated by target circles.

Referring first to FIGS. 1, 2 and 3, a first embodiment of a vibration dampening device 10 has a strap 12 with a proximal end 14 and a distal end 16. The strap 12 defines a length and a width and a longitudinal axis A, wherein the strap length is longer than the strap width. As fastening means, a hook strip 18 is attached to a body contacting surface 22 of the strap 12, and a loop strip 20 is attached to the outer surface 24 of the strap 12. The strips 18, 20 shown in FIGS. 1 to 3 were medium hook and felt VELCRO® hook loop fasteners, obtained from Velcro USA Inc. of Manchester, N.H. The strips 18, 20 preferably are attached with an elastomeric adhesive that can stretch when subjected to tensile force without de-adhering. One adhesive that meets these conditions is a VELCRO® adhesive. Another adhesive is ALCOTE 532, available from Rohm and Haas Company, Philadelphia, Pa. Alternatively, strips 18, 20 may be attached by stitching with an elastomeric thread.

Alternative fastening means may be used (not shown) to hold the strap into place, including a buckle, or cinch or a series of snaps or hooks. It is also possible to custom-make integral continuous straps formed into a loop or band to fit various body parts. However, it is preferred that fastening means are used, and that such fastening means allow a wearer to adjust the wrapping tension.

In FIGS. 1 and 2, the strap 12 is shown in an open condition, not wrapped around a human body part. When wrapped around a human body part, such as a forearm or upper arm or an ankle, calf or thigh, the hook strip 18 engages the loop strip 20 to secure the strap 12 to such body part.

Preferably, the strap 12 is formed from a stretchable or viscoelastic material 40, such as neoprene, polyethylene, polyurethane or spandex. Most preferably, the body contacting surface 22 of the strap 12 is covered with a woven or nonwoven fabric or covering so that the strap may be comfortably worn over a body part. Even more preferably, the outer surface of the strap 12 also comprises a woven or nonwoven fabric or covering. Suitable materials for the woven or nonwoven fabric or covering comprise nylon or rayon or DACRON® (trademark of E.I. DuPont de Nemours & Company) or GORE-TEX® (trademark of W. L. Gore & Associates). Other coverings include blends of synthetic and natural fibers, such as cotton, nylon, rayon blends. Particularly preferred materials for the strap 12 are laminate structures having a viscoelastic material sandwiched between two woven fabric layers, such as polymer materials made by Rubberite, including R-1400-N, a neoprene polymer material that has an elongation of 200%, 4219-NEU, a neoprene polymer material that has an elongation of 130%, G231-N, a neoprene polymer material that has an elongation of 450%, SCE43B, a neoprene/EPDM/SBR polymer material that has an elongation of 150%, ENSOLITE IV2, a neoprene/PVC/Nitrile polymer material that has an elongation of 100%, and HYPUR-CE T-0805, a polyurethane polymer material that has an elongation of 100%. One particularly preferred material, R-1400-N, is shown best in FIG. 3, in which a viscoelastic material 40 is sandwiched between two woven fabric or covering layers 42 to form a laminate structure. A preferred thickness for the strap is from 0.158 to 2.54 cm (1/16 to 1 inch), and most preferably is about 0.31 cm (1/8 inch). Thickness may vary depending upon body location for best form, fit and function.

Preferred stretchable or viscoelastic materials for forming the strap 12 have the following properties as set forth in Table I:

TABLE I

| Physical property | Unit of Measure | Range |
| --- | --- | --- |
| Compression deflection @25% | psi | 3 to 10 |
| Density | Lbs/ft$^3$ | 7 to 15 |
| Tensile Strength | psi | 40 to 80 |

TABLE I-continued

| Physical property | Unit of Measure | Range |
| --- | --- | --- |
| Elongation (minimum to maximum) | % | 100 to 450 |
| Temperature range | ° F. | −70 to +250 |
| Force constant (k = F/x) | Lbs/inch | 0.1 to 5.0 |

Referring again to FIGS. 1, 2 and 3, in the first embodiment of the dampening device a first step member 26 is engaged to the body contacting surface 22 of the strap 12, such as with adhesive. A preferred adhesive is ALCOTE 532 from Rohm and Haas Company. Alternate engaging methods are possible, such as, but not limited to, hook and loop fasteners, stitching with elastomeric thread, buttons, grommets, rivets or staples. The first step member 26 has a length and width, with its length greater than its width and further with its width the same as or shorter than the width of the strap 12. The first step member 26 further defines an axis along its length. The first step member 26 is aligned such that its axis is parallel to or generally aligned with the axis A of the strap 12.

A second step member 26a is engaged to the body contacting surface 22 of the strap 12, such as with adhesive. Alternate engaging methods are possible, such as, but not limited to, hook and loop fasteners, stitching with elastomeric thread, buttons, grommets, rivets or staples. The second step member 26a has a length and width, with its length greater than its width and further with its width the same as or shorter than the width of the strap 12. The second step member 26a further defines an axis along its length. The second step member 26a is aligned such that its axis is parallel to or generally aligned with the axis A of the strap 12. The second step member 26a is spaced apart from the first step member 26 such that there is a gap therebetween.

An additional step member 32 is engaged to the outer surface of the second step member 26a, such as with adhesive or an acceptable alternate engaging method. The additional step member 32 has a length and a width, with its length greater than its width. The additional step member 32 further defines an axis along its length. The additional step member 32 is positioned such that its axis is parallel to or generally aligned with the axis A of the strap 12. In addition, the additional step member 32 is off-set from the second step member 26a such that one end of the additional step member 32 is not engaged to the second step member 26a or to the surface 22 of the strap 12 and extends beyond the end of the second step member 26a. Preferably, the one extending end extends from 0.05 to 1 inch from the edge of the strap 12. The one extending end of the additional step member 32 has freedom to move with relation to the second step member 26a. By "freedom to move" or "freedom of movement" is meant that the one extending end of the additional step member 32 may flexibly oscillate upwards and downwards or closer to and farther from the body contacting surface 22 of the strap 12. The additional step member 32 may also be referred to herein as an "axial additional step member" in view of its alignment generally with the longitudinal axis A of the strap 12.

As shown in FIGS. 1, 2 and 3, a further additional step member 34 is attached to the outer surface of the first step member 26, such as with adhesive or an acceptable alternate attaching or engaging method. The further additional step member 34 has a length and a width, with its length greater than its width. The further additional step member 34 further defines an axis along its length. The further additional step member 34 is positioned such that its axis is at an angle to the axis A of the strap 12. Preferably, the further additional step member 34 is positioned so that its axis is generally perpendicular to the axis A of the strap 12. The further additional step member 34 is off-set from the step member 26 such that at least one end of the further additional step member 34 is not engaged to the first step member 26 or to the surface 22 of the strap 12 and extends beyond the side edge of the step member 26. The at least one extending end of the further additional step member 34 has freedom to move with relation to the step member 26. Most preferably, the further additional step member 34 is positioned such that both ends of the further additional step member 34 are not engaged to the first step member 26 or to the surface 22 of the strap 12 and extend beyond the side edge of the step member 26. Thus in this most preferred embodiment (as is shown in FIGS. 1, 2 and 3), both ends of the further additional step member 34 have freedom to move with relation to the step member 26. The further additional step member 34 may also be referred to herein as a "radial additional step member" in view of its alignment generally at an angle to, and preferably perpendicular to, the longitudinal axis A of the strap 12.

The additional step member 32 may be of the same or different length as the length of the further additional step member 34. The additional step member 32 may be of the same or different width as the width of the further additional step member 34.

Most preferably, the step members 26, 26a and the additional step members 32, 34 are formed from the same stretchable or viscoelastic material(s) as the strap 12. Such step members 26, 26a, 32 and 34 may also be covered on one or both surfaces with a woven or nonwoven fabric material. The step members 26, 26a, 32 and 34 may be of the same or different thickness, and may be of the same or different thickness from the strap 12. Preferably, the thickness of the step members 26, 26a, 32 and 34 is in the range of 0.158 to 2.54 cm (1/16 to 1 inch), and most preferably is 0.317 cm (1/8 inch).

The strap 12 may be wrapped about a forearm (for example), so that the fasteners 16, 18 are engaged and the skin contacting surface 22 is in contact with the forearm skin. The strap 12 is tightened to a suitable tension (such as 0.1 to 5 pounds-force, preferably 1 to 3 pounds-force) to maintain the strap in position on the forearm and to hold the step members 26, 26a, 32 and 34 in position. The strap 12 is not wrapped so tightly as to become a tourniquet that limits blood flow. The step members 26, 26a serve to hold the strap 12 off the skin and provide a gap so that the strap 12 is more easily engaged at a suitable wrapping tension that will not impose undue local pressure on body tissue.

Referring next to FIGS. 4 and 5, a second or alternate embodiment of the vibration dampening device 10b is shown, wherein like reference numerals refer to like elements. In such alternate embodiment, a strap 12a with a proximal end 14 and a distal end 16 defines a length and a width and a longitudinal axis. The strap length is longer than the strap width. As fastening means, a hook strip 18 is attached to a body contacting surface 22 of the strap 12a, and a loop strip 20 is attached to the outer surface 24 of the strap 12a. As with the embodiment of FIGS. 1 to 3, alternative fastening means may be used (not shown), including but not limited to a buckle, a cinch or a series of snaps or hooks or buttons. Such strap may also be formed as a continuous loop without fasteners, although it is preferred to have fasteners so that the wrapping tension may be adjusted. In FIGS. 4 and 5, the strap 12a is shown in an open condition, not wrapped around a human body part. When wrapped around a human body part, such as a forearm or upper arm, or ankle, calf or thigh, the hook strip 18 engages the loop strip 20 to secure the strap 12a to such body part.

First and second radial step members 30 are attached to or engaged to the body contacting surface 22 of the strap 12a, such as with adhesive or other acceptable attachment means. The first and second radial step members 30 define a length and a width wherein the length is greater than the width. Such step member 30 length is also greater than the width of the strap 12a. The first and second radial step members 30 are spaced apart from one another so as not to be in contact with one another. In FIG. 5, there is a defined gap 36 between first and second radial step members 30. The step members 30 are shown disposed in generally parallel relation wherein the longitudinal axis of the first step member 30 is generally parallel to the longitudinal axis of the second step member, and both such axes are generally perpendicular to the longitudinal axis of the strap 12a. While it is preferred to position such step members 30 in substantially parallel relation to each other and substantially perpendicular to the longitudinal axis of the strap 12a, it is also possible to engage the step members 30 to the body contacting surface 22 of the strap at angles within the range of 15 to 165 degrees, preferably from 45 to 135 degrees.

The ends of the first and second radial step members 30 are not engaged to the strap 12a. Such ends thus have freedom to move with relation to the body contacting surface 22 of strap 12a. By "freedom to move" is meant that the extending ends of the step member 30 may flexibly oscillate upwards and downwards or closer to and farther from the body contacting surface 22 of the strap 12a. As shown in FIG. 5, both ends of both step members 30 have freedom to move. However, it is also possible to align the step members 30 so that only one end has freedom to move.

A further or third embodiment 10c of the invention is shown in FIGS. 6 and 7. In this embodiment, a first radial step member 30a has shorter length than a second radial step member 30b. In addition the defined gap 36a between the step members 30a, 30b is shorter than the gap 36 between step members 30 in the embodiment shown in FIGS. 4 and 5. The strap 12c has a lesser thickness than the thickness of the strap 12 of the embodiments shown in FIGS. 1 to 3 and 12a in FIGS. 4 and 5. This third embodiment 10c is more suited for wrapping a wrist or an upper or a lower arm having a smaller circumference.

Yet another or fourth embodiment 10d of the vibration dampening device according to the invention is shown in FIGS. 8 and 9. In this embodiment, the strap 12 has a single radial step member 30 engaged or attached to the body contacting surface 22 and opposite to the surface onto which the hook strip 18 for the fastening means has been applied. The radial step member 30 is shown attached at or very near the proximal end of the strap 12. However, such single radial step member 30 might alternatively be positioned at any point along the length of the strap 12. As shown in FIG. 9, the ends of the single radial step member 30 are not attached to the body contacting surface 22 of the strap 12 so as to have freedom of movement with relation to the strap 12. It is also possible to position the single radial step member 30 so that only one end has freedom of movement, or such that the longitudinal axis of the radial step member 30 is not substantially perpendicular to the longitudinal axis of the strap 12.

FIG. 10 shows still another or fifth embodiment 10e of the vibration dampening device in which the strap 12e is of a much shorter length than the straps 12 shown in FIGS. 1 to 3 and 4 and 5. Such strap 12e also is thinner than the straps 12 depicted in FIGS. 1 to 3 and 4 and 5. One radial step member 30 is attached or engaged to the body contacting surface 22 at a central portion of the strap 12e. Such single radial step member has at least one end with freedom of movement in relation to the strap 12e. This fifth embodiment 10e is particularly suited for wrapping a toe or a finger.

Yet another or sixth embodiment 10f is shown in FIGS. 11 and 12. In this embodiment 10f two axial step members 26 are attached or engaged to the body contacting surface 22 of the strap 12f, such as with adhesive or other alternate engaging means. The step members 26 each have a length and width, with length greater than width, and further with width the same as or shorter than the width of the strap 12f. The step members 26 each further define a central axis along their respective length. As shown in FIG. 12, step members 26 are aligned such that each respective axis is parallel to or generally aligned with the axis of the strap 12f. The step members 26 are further spaced apart from one another such that they do not contact one another, but leave a gap therebetween. The axial step members 26 are shown in FIG. 11 to have the same thickness as strap 12f, which is preferred. However, the axial step members 26 may be of different thickness than strap 12f.

Referring next to FIGS. 13 and 14, yet another alternate or seventh embodiment of the vibration dampening device is shown. In this embodiment, a strap 60 has a proximal end 62 and a distal end 64. A hook strip 66 at the proximal end 62 may be engaged with a loop strip 68 at the distal end 64 so as to secure the strap 60 around a body part. The strap 60 defines a length and a nominal width and an axis along its length. The strap 60 is formed with integral wing sections 70, 72 that extend beyond the nominal width and have freedom of movement with respect to the strap portion within the nominal width. As shown in FIG. 14, wing sections 72 are aligned such that they extend from the strap from opposite sides at the same or nearly the same position along the longitudinal axis of the strap 60. In contrast, wing sections 70 extend from the strap 60 at different positions along the longitudinal axis of the strap 60. While the embodiment shown in FIGS. 13 and 14 has a combination of aligned wing sections 72 and non-aligned wing sections 70, it is within the scope of the invention to include only aligned wing sections 72 or only non-aligned wing sections 70, or any combination thereof. While the wing sections 70, 72 are shown to have an equivalent length extending beyond the nominal width of the strap 60, it is within the scope of the invention to have wing sections extend different lengths. A preferred range of lengths for such wing sections 70 or 72 is from 0.05 to 1 inch.

The vibration dampening devices according to the invention may be applied around a number of different body parts at a number of different positions to help dampen vibrations that travel through soft tissue and musculature. For example, the vibration dampening devices may be wrapped around a finger, a thumb, a wrist, a forearm, an upper arm, a neck, a chest, a waist, a torso, an ankle, a lower leg or calf, and an upper leg or thigh. Various possible wrap locations are shown by target dots on a schematic drawing of a human body in FIG. 17. Vibration dampening devices 90, 92, 94, 96, 98, 99 and 100 are wrapped around various body parts of the human body shown in FIG. 17. A device 90 is wrapped around the wrist. A device 92 is wrapped around the upper arm between the shoulder and the elbow. A device 94 is wrapped around a finger. A device 96 is wrapped around a thumb. A device 98 is wrapped around a thigh. A device 99 is wrapped around a chest or torso. A device 100 is wrapped around an ankle. FIG. 17 is not intended to be limiting. The dampening devices may be worn one at a time or in various combinations. When wrapped, the tension preferably should be maintained at or below 5 pounds-force, more preferably in the range of 1 to 5 pounds-force, most preferably at or below 3 pounds-force (i.e., 32 psi for a strap that is 0.75 inches wide and ⅛ inch thick or 0.093 square inches in surface area) to dampen vibrations from continuing to travel longitudinally along the soft tissue and musculature beyond the device.

Table II below sets out exemplary dimensions for various vibration dampening straps according to the invention. These dimensions are preferred, but are not required.

TABLE II

| Body part | Maximum Strap Length (in) | Strap Width (in) | Strap Thickness (in) | Wing Flap Length (in) | Wing Thickness (in) |
|---|---|---|---|---|---|
| Wrist | 10 | 0.25 to 2.0 | 0.1 to 0.5 | 0.05 to 1.0 | 0.05 to 0.5 |
| Forearm | 13 | 0.25 to 2.0 | 0.1 to 0.5 | 0.05 to 1.0 | 0.05 to 0.5 |
| Upper arm | 14 | 0.25 to 2.0 | 0.1 to 0.5 | 0.05 to 1.0 | 0.05 to 0.5 |
| Ankle | 11 | 0.25 to 2.0 | 0.1 to 0.5 | 0.05 to 1.0 | 0.05 to 0.5 |
| Calf | 18 | 0.25 to 2.0 | 0.1 to 0.5 | 0.05 to 1.0 | 0.05 to 0.5 |
| Thigh | 24 | 0.25 to 2.0 | 0.1 to 0.5 | 0.05 to 1.0 | 0.05 to 0.5 |
| Finger | 3 | 0.1 to 1.0 | 0.1 to 0.5 | 0.05 to 0.5 | 0.05 to 0.5 |
| Thumb | 4 | 0.1 to 1.0 | 0.1 to 0.5 | 0.05 to 0.5 | 0.05 to 0.5 |
| Large toe | 4 | 0.1 to 1.0 | 0.1 to 0.5 | 0.05 to 0.5 | 0.05 to 0.5 |
| Small toes | 3 | 0.1 to 1.0 | 0.1 to 0.5 | 0.05 to 0.5 | 0.05 to 0.5 |
| Chest | 50 | 0.25 to 6.0 | 0.1 to 0.5 | 0.05 to 1.0 | 0.05 to 0.5 |
| Neck | 20 | 0.25 to 1.0 | 0.1 to 0.5 | 0.05 to 1.0 | 0.05 to 0.5 |
| Waist | 40 | 0.25 to 4.0 | 0.1 to 0.5 | 0.05 to 1.0 | 0.05 to 0.5 |

It may be difficult for individual wearers to gauge whether or not they have wrapped the vibration dampening devices according to the invention with sufficient tension, but not so tightly as to achieve the benefits intended. As shown in FIGS. 15 and 16, a tension limiter 80 optionally may be incorporated into the structure of the device. The tension limiter 80 shown in FIGS. 15 and 16, is a loop 86 with a first end 82 and a second end 84. The first and second ends 82, 84 are attached to the body contacting surface 22 of the strap 12 such that the loop portion remains loose when the strap is not tightened to an overly taught condition, such as in excess of 32 pounds per square inch. This looser condition is shown in FIG. 15. Attachment of the ends 82, 84 may be with adhesive or stitching or other comparable attaching means. Alternatively, the ends 82, 84 may be attached to the outer surface of the strap 12 (not shown in FIGS. 15 and 16). As the strap 12 is tightened around a body part to a taught condition, such as up to about 3 pounds-force (which translates to 32 psi over an area of 0.093 square inches), the tension limiter 80 stretches and the loop portion is no longer as loose as shown in FIG. 15. In the taught condition at the maximum desired tension, the loop portion 86 contacts the body contacting surface 22 of the strap 12 and the tension limiter 80 reaches a maximum stretch condition. The tension limiter 80 thus resists further stretching of the strap 12, helping to maintain the tension at or just below the maximum level.

Figure 18:
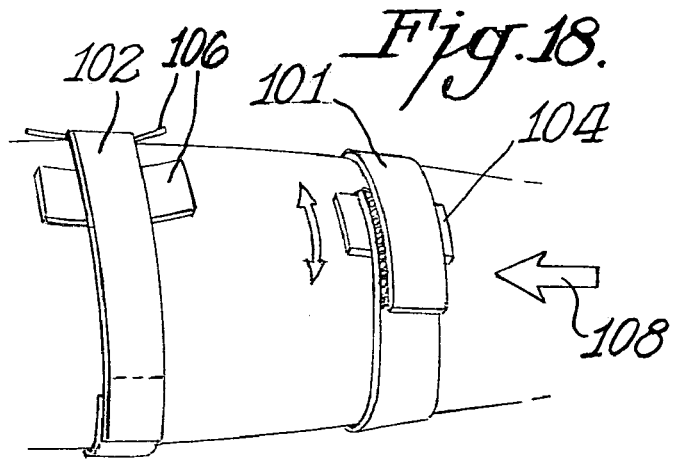
FIG. 18 is a perspective view of a human forearm having two vibration dampening straps according to the invention wrapped thereon.

The vibration dampening devices according to the invention may be used singly or in combination to dampen vibrations of soft tissue or musculature. Referring to FIG. 18, a first vibration dampening device according to the invention 101 and a second vibration dampening device according to the invention 102 are shown as wrapped around a human forearm. The first device 101 has a radial step member 104 of a first length. The second device 102 has two radial step members 106 having a length longer than the first length of step member 104. As a vibration, such as from an impact of a ball hitting a racket, travels through soft tissue in the direction of arrow 108, the ends of radial step member 104 have freedom of movement relative to the strap portion of device 101 to help dampen such vibration. Similarly, the ends of radial step members 106 have freedom of movement relative to the strap portion of device 102 to further dampen any vibrations that have continued to travel past device 101 to device 102.

Referring next to FIG. 19, another alternate embodiment or eighth embodiment 10g of the vibration dampening strap of the invention is shown. In this eighth embodiment 10g the strap has three wings 114, 116, 118 extending beyond the width of the strap. As shown in FIG. 19, the wings are spaced equidistant from one another, and have central axes generally perpendicular to the central axis of the strap. Alternate arrangements wherein the wings are spaced apart at varying distances, or have varying angular orientation with respect to the central axis of the strap are possible. In addition the wings have equivalent lengths in FIG. 19, although this is not required. Preferably, the central wing 116 has a different force constant k than the wings 114, 118. By including a wing 116 with a different force constant, the vibration dampening strap of the invention 10g has better ability to dampen vibrations of varying frequencies and amplitudes that travel along the soft tissue. The force constant of a wing may be varied by using different material to construct the wing, or by varying the thickness or shape of the outer periphery of the wing.

As one example, the force constant (k) of the material selected for wing 116 is from 0.5 to 2 lb/in$^2$, whereas the force constant (k) for the material selected for wings 114, 118 is from 2 to 5 lb/in$^2$. Use of materials with different force constants for the wings allows the vibration dampening device to better respond to vibrations having different frequencies and amplitudes.

FIG. 20 shows a ninth embodiment 10f of the vibration dampening strap of the invention that has three wings 122. Wings 122 have curved or semi-circular outer edges, which may offer enhanced vibration dampening as compared to wings with straight outer edges such as shown in FIG. 19. Alternate wing edge geometries are possible; and are within the scope of the invention. In addition, while wing members have been shown with uniform thicknesses, wing thickness may vary along wing length. For example, wing edges may be thicker than central wing portions, or wing outer periphery shapes may be different for adjacent wings by varying thickness of the material.

While not wishing to be bound by any one theory, FIG. 21 is a diagram to illustrate how the vibration dampening straps according to the invention are believed to function. The vibration dampening strap 130 is shown in phantom outline and has a wing 132 (also shown in phantom outline) attached to the body-contacting surface of the strap 130 with edges extending beyond the width of the strap 130. The strap 130 is attached to a human forearm represented schematically by a bone 134, soft tissue or musculature 136, and skin 138. A shock or vibration travels longitudinally in the direction from left to right as indicated by arrow 140. The longitudinal vibration wave has a first amplitude ($\Delta Y_L$). Another shock or vibration travels radially outwardly from the bone as indicated by arrow 142. This radial vibration wave has a first amplitude ($\Delta Y_R$).

The vibration dampening strap 130 of the invention is a passive mechanical vibration dampening device. Vibrations in musculature and soft tissue generally have frequencies from less than 1 to about 500 cycles per second (Hz) and amplitudes from less than 1 mm (e.g., in muscular areas) to over 25 mm (e.g., in fatty soft tissue areas). Tissue movement in both amplitude and frequency commonly leads to pain or injury. The strap 130 counters radially traveling vibrations by supporting the skin and soft tissue in an area. The strap 130 in combination with the wing 132 best counters longitudinally traveling vibrations.

The strap 130 holds the wing 132 in contact with the skin 138, but is not wrapped so tightly as to apply a tourniquet force to the arm. When the longitudinal vibration meets the vibration dampening strap 130, the edges of the wing 132 may move freely to apply counter forces opposite to the vibration amplitude to help restore the skin and tissue to the pre-shocked position. That the ends of the wings extending from the width of the strap may move freely is an important feature of this embodiment of the invention. The restoring force F is calculated as F=k*x, where k (force constant) is from 0.1 to 5 pounds/inch and x is the displacement distance moved by the wing. The wings thus apply a restoring force to counter the longitudinal vibration. As shown in FIG. 21, the amplitude of the longitudinally traveling vibration has been reduced from $\Delta Y_L$ to a lesser amplitude (seen to the right of the strap 130) after the vibration has traveled past the strap 130 and a restoring force has been applied by the wing 132.

For example, if wing movement induced by vibration is translated to be linear movement (x) of 0.1 inch, and the k value for the wing material is 2 pounds/inch, then the restoring force F is calculated as 2 pounds/inch times 0.1 inch or 0.2 pounds-force. If the vibration dampening device has three wings extending only from one side of a strap, and if the wings have equivalent k value, the restoring force F is 3 times 0.2 pounds-force or 0.6 pounds-force. If the three wings extend from both sides of the strap, the restoring force F is doubled to 1.2 pounds force.

If multiple wings each formed of a material with a different modulus of elasticity (and thus different force constant) are used in combination, a variety of restoring forces to counter longitudinal vibrations are applied. Under Hooke's law, within the elastic limit, deformation produced is proportional to the stress.

The invention has been illustrated by detailed description and examples of the preferred embodiments. Various changes in form and detail will be within the skill of persons skilled in the art. Therefore, the invention must be measured by the claims and not by the description of the examples or the preferred embodiments.

We claim:

1. A vibration dampening device for wrapping a human body part, comprising:
a strap defining a central axis, having a nominal width and having a body contacting surface and an outer surface;
a step member engaged to the strap, wherein said step member has a length and a width, and the length of said step member is longer than the width of said step member, and further wherein the length of the step member is longer than the width of the strap and the proximal and distal ends of the step member are free from a fastener, and further wherein said step member is formed from a stretchable material, and still further wherein said step member defines an axis along its length, and said step member is engaged to the body contacting surface of the strap so that its axis is at an angle with respect to the axis of the strap, said angle ranging between 15 and 165 degrees.

2. The device of claim 1, wherein the axis of the step member is substantially perpendicular to the axis of the strap.

3. The device of claim 2, wherein the step member defines a first wing portion at its distal end and a second wing portion at its proximal end, and wherein the first wing portion extends beyond the width of the strap when the step member is engaged to the strap.

4. The device of claim 1, wherein the strap defines a central axis and the step member defines an axis along its length, and said step member is engaged to the body contacting surface of the strap so that its axis is either parallel to or generally aligned with the axis of the strap.

5. The device of claim 4, further comprising a second step member defining an axis along its length and engaged to said step member so that its axis is either parallel to or generally aligned with the axis of said step member.

6. The device of claim 4, further comprising a second step member defining an axis along its length and engaged to said step member so that its axis is substantially perpendicular to the axis of said step member.

7. The device of claim 1, further comprising one or more additional step members engaged to the body contacting surface of the strap.

8. The device of claim 7, wherein at least one of the additional step members has a modulus of elasticity different from the step member.

9. The device of claim 7, wherein said step member and said additional step member(s) are disposed along the strap so as not to contact one another.

10. The device of claim 9, wherein said step member and said additional step member(s) are disposed along the strap so as to define a gap between each adjacent step member of from 0.25 to 4.0 inches.

11. The device of claim 1, wherein the strap defines a proximal end and a distal end, and further comprising means for detachably securing the distal end of the strap to the proximal end of the strap.

12. The device of claim 11, wherein the means for detachably securing the distal end of the strap to the proximal end of the strap comprises a hook and loop fastener wherein a hook portion is provided on the body contacting surface at the proximal end of the strap and a loop portion is provided on an outer surface at the distal end of the strap.

13. The device of claim 1, wherein the strap comprises at least in part a material selected from the group consisting of neoprene, polyethylene, polyurethane and spandex.

14. The device of claim 13, further comprising a woven or non woven fabric or felt covering forming the body contacting surface of the strap.

15. The device of claim 14, further comprising a woven or nonwoven fabric or felt covering forming the outer surface of the strap.

16. The device of claim 13, wherein the step member comprises the same at least one material as the strap.

17. The device of claim 1, wherein the step member is engaged to the body contacting surface with an adhesive.

18. The device of claim 1, wherein the strap comprises a viscoelastic material having a density in the range of 7 to 15 pounds per cubic foot, a tensile strength from 40 to 80 psi and a minimum elongation of 100%.

19. The device of claim 18, wherein the viscoelastic material has a compression deflection at 25% of from 3 to 10 psi.

20. The device of claim 1, wherein said at least one step member is viscoelastic.

21. The device of claim 1, wherein the strap when wrapped around a human body part exerts a tension of no more than 5 pounds-force on said human body part.

22. The device of claim 1, further comprising a tension limiter formed by attaching a loop to the strap.

23. The device of claim 22, wherein said loop has two ends and a loop portion between said ends, and wherein said ends are attached to the body contacting surface of the strap when the loop is in relaxed condition and the strap is not under tension.

24. The device of claim 23, wherein a first wing section is spaced apart from a second wing section so as to define a gap between of from 0.25 to 4.0 inches.

25. The device of claim 23, wherein the strap has a proximal end and a distal end and means for detachably securing the distal end to the proximal end of the strap.

26. The device of claim 25, wherein the means for detachably securing the distal end to the proximal end of the strap comprises a hook and loop fastener, wherein a hook portion is provided on the body contacting surface at the proximal end of the strap and a loop portion is provided on the outer surface at the distal end of the strap.

27. The device of claim 23, wherein the strap comprises at least one material selected from the group consisting of neoprene, polyethylene, polyurethane and spandex.

28. The device of claim 27, further comprising a woven or nonwoven fabric or felt covering forming the body contacting surface of the strap.

29. The device of claim 28, further comprising a woven or nonwoven fabric or felt covering forming the outer surface of the strap.

30. The device of claim 23, wherein the strap is formed from a viscoelastic material having a density in the range of 7 to 15 pounds per cubic foot, a tensile strength from 40 to 80 psi, and a minimum elongation of 100%.

31. The device of claim 30, wherein the viscoelastic material has a compression deflection at 25% of from 3 to 10 psi.

32. A method for dampening vibration of soft tissue or musculature of a human wearer's body part, comprising:
providing a stretchable strap having a nominal width and having a body contacting surface and an outer surface, wherein said strap defines a central axis along its length, and wherein a step member is engaged to the stretchable strap, wherein said step member has a length and a width, and the length of said step member is longer than the width of said step member, and further wherein the length of the step member is longer than the width of the stretchable strap, and still further wherein said step member defines an axis along its length, and said step member is engaged to the strap so that axis of the step member is at an angle between 15 degrees and 165 degrees with respect to the axis of the strap;
providing a tension limiter comprising a loop attached to said strap;
wrapping the stretchable strap around the body part so that the body contacting surface is in contact with the wearer's skin and the stretchable strap is under tension.

33. The method of claim 32, wherein the stretchable strap exerts a tension of no more than 5 pounds-force.

34. The method of claim 32, wherein the stretchable strap exerts a tension of from 0.1 to 5 pounds-force.

35. The method of claim 32, wherein the strap has a proximal end and a distal end and has a means for adjustably fastening the proximal end to the distal end.

36. The method of claim 32, wherein the step member is engaged to the body contacting surface of the strap.

37. The method of claim 36, wherein one or more additional step members are engaged to the strap and are disposed along the strap in spaced apart relation so as not to contact one another.

38. The method of claim 36, wherein at least one of the additional step members has a modulus of elasticity different from the step member.

39. The method of claim 32, wherein a second step member defining an axis along its length is engaged to said step member so that the axis of the second step member is parallel to or generally aligned with an axis defined by the step member.

40. The method of claim 32, wherein the strap is wrapped around a body part selected from the group consisting of: thumb, finger, wrist, forearm, upper arm, toe, ankle, lower leg, thigh, torso and neck.

41. The method of claim 32, wherein the step member defines a wing portion that extends beyond the width of the strap when the step member is engaged to the strap.

42. A vibration dampening device for wrapping a human body part, comprising:
 a strap having a nominal width and a length, and having a body contacting surface and an outer surface, said strap furthermore defining an axis along its length;
 a step member engaged to the strap, wherein said step member has a length and a width, and wherein the length of said step member is longer than the width of said step member, and further wherein the length of the step member is longer than the width of the strap, and still further wherein said step member has proximal and distal ends that extend beyond the nominal width of the strap, and has freedom of movement with respect to said strap, and still further wherein said step member defines an axis along its length, and said step member is engaged to the strap so that axis of the step member is at an angle between 15 decrees and 165 degrees with respect to the axis of the strap.

43. The device of claim 42, wherein the step member is engaged to the outer surface of the strap.

44. The device of claim 42, wherein the step member is engaged to the body contacting surface of the strap.

45. The device of claim 42, wherein at least one of said proximal and distal end terminates in a semi-circular shape.

46. The device of claim 42, wherein said at least one step member is viscoelastic.

* * * * *